(12) United States Patent
Fink et al.

(10) Patent No.: US 7,410,485 B1
(45) Date of Patent: Aug. 12, 2008

(54) DIRECTIONAL MICROWAVE APPLICATOR AND METHODS

(75) Inventors: Patrick W. Fink, Missouri City, TX (US); Greg Y. Lin, Friendswood, TX (US); Andrew W. Chu, Friendswood, TX (US); Justin A. Dobbins, Houston, TX (US); G. Dickey Arndt, Friendswood, TX (US); Phong H. Ngo, Friendswood, TX (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 640 days.

(21) Appl. No.: 11/040,613

(22) Filed: Jan. 14, 2005

(51) Int. Cl.
*A61B 18/04* (2006.01)
*A61N 1/06* (2006.01)

(52) U.S. Cl. .................. 606/33; 607/156

(58) Field of Classification Search .......... 606/32, 606/33, 38–41; 607/101, 102, 154, 156
See application file for complete search history.

(56) References Cited

U.S. PATENT DOCUMENTS

| | | | |
|---|---|---|---|
| 4,204,549 A | 5/1980 | Paglione | |
| 4,311,154 A | 1/1982 | Sterzer et al. | |
| 4,532,924 A * | 8/1985 | Auth et al. | 606/50 |
| 4,601,296 A | 7/1986 | Yerushalmi | |
| 4,776,086 A | 10/1988 | Kasevich et al. | |
| 5,026,959 A | 6/1991 | Ito et al. | |
| 5,131,409 A * | 7/1992 | Lobarev et al. | 607/156 |
| 5,151,100 A | 9/1992 | Abele et al. | |
| 5,186,171 A * | 2/1993 | Kuhry | 607/68 |
| 5,314,466 A | 5/1994 | Stern et al. | |
| 5,323,778 A | 6/1994 | Kandarpa et al. | |
| 5,370,644 A | 12/1994 | Langberg | |
| 5,694,134 A | 12/1997 | Barnes | |
| 5,843,144 A | 12/1998 | Rudie et al. | |
| 5,904,709 A | 5/1999 | Arndt et al. | |
| 6,245,062 B1 | 6/2001 | Berube et al. | |
| 6,289,249 B1 | 9/2001 | Arndt et al. | |
| 6,383,182 B1 | 5/2002 | Berube et al. | |
| 6,496,736 B1 | 12/2002 | Carl et al. | |
| 6,527,768 B2 | 3/2003 | Berube | |
| 6,690,963 B2 | 2/2004 | Ben-Haim et al. | |
| 2002/0128642 A1 | 9/2002 | Berube et al. | |
| 2005/0228370 A1 * | 10/2005 | Sterzer et al. | 606/33 |

OTHER PUBLICATIONS

K. C. Bupta et al., "Microstrip Lines and Slotlines," 1996, published by Artech House, in Norwod Massachusetts, Chapter 7.
K. L. Wong et al., "Design by Nnplanar Microstrip Antennas and Transmission Lines," 1999, published by John Wiley & Sons, Inc., NY, NY, Chapter 8.

* cited by examiner

*Primary Examiner*—Michael Peffley
(74) *Attorney, Agent, or Firm*—Theodore U. Ro

(57) ABSTRACT

A miniature microwave antenna is disclosed which may be utilized for biomedical applications such as, for example, radiation induced hyperthermia through catheter systems. One feature of the antenna is that it possesses azimuthal directionality despite its small size. This directionality permits targeting of certain tissues while limiting thermal exposure of adjacent tissue. One embodiment has an outer diameter of about 0.095" (2.4 mm) but the design permits for smaller diameters.

20 Claims, 11 Drawing Sheets

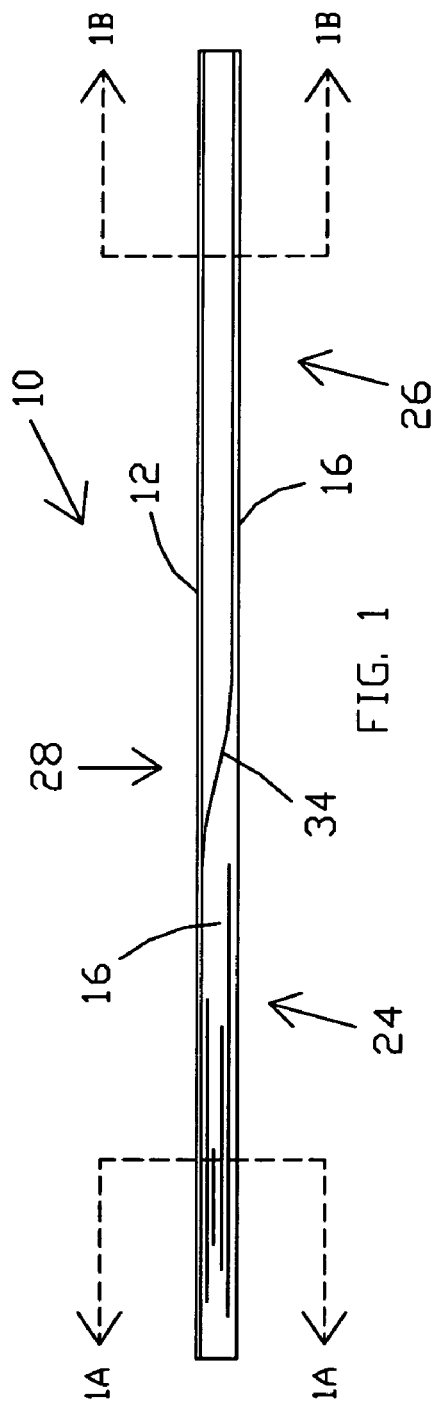
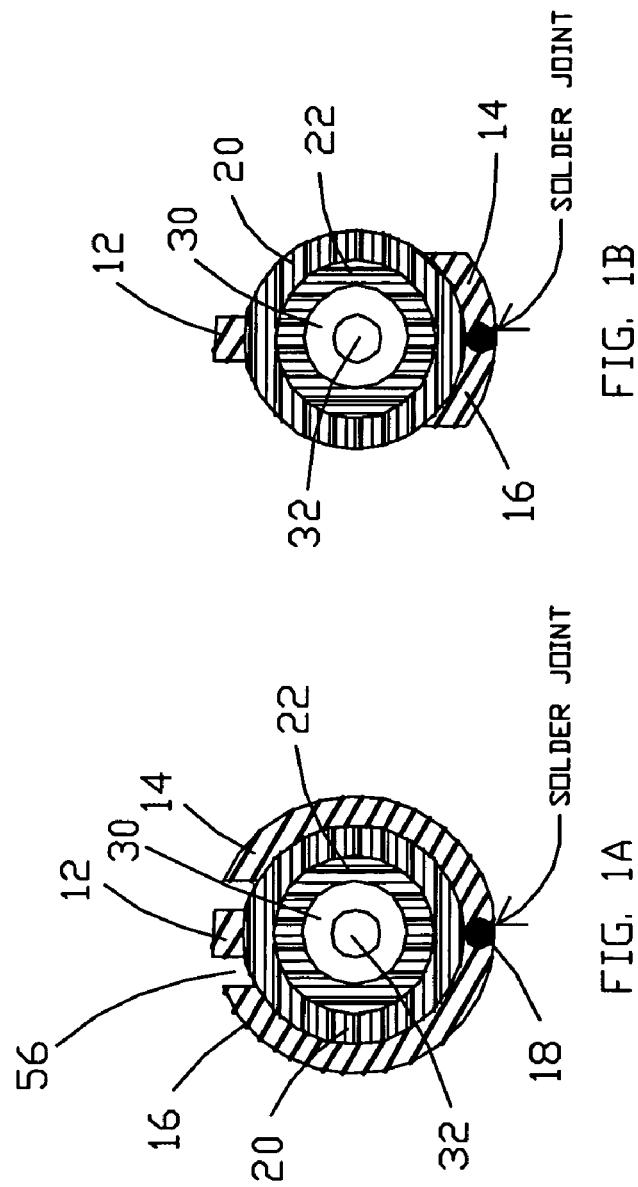
FIG. 1
FIG. 1A
FIG. 1B

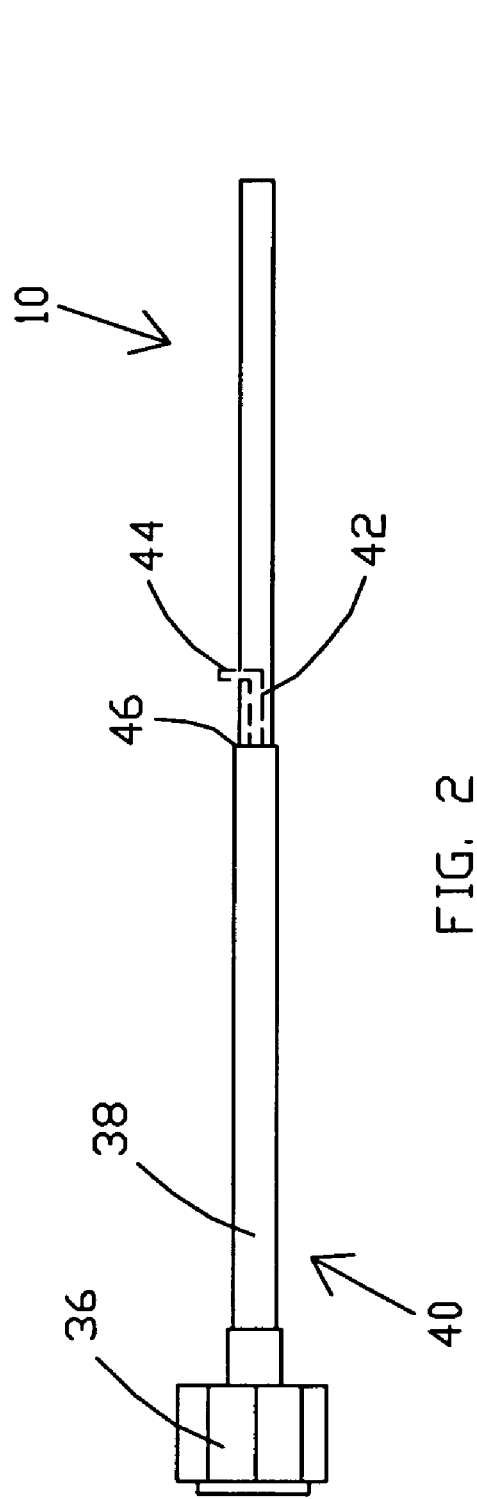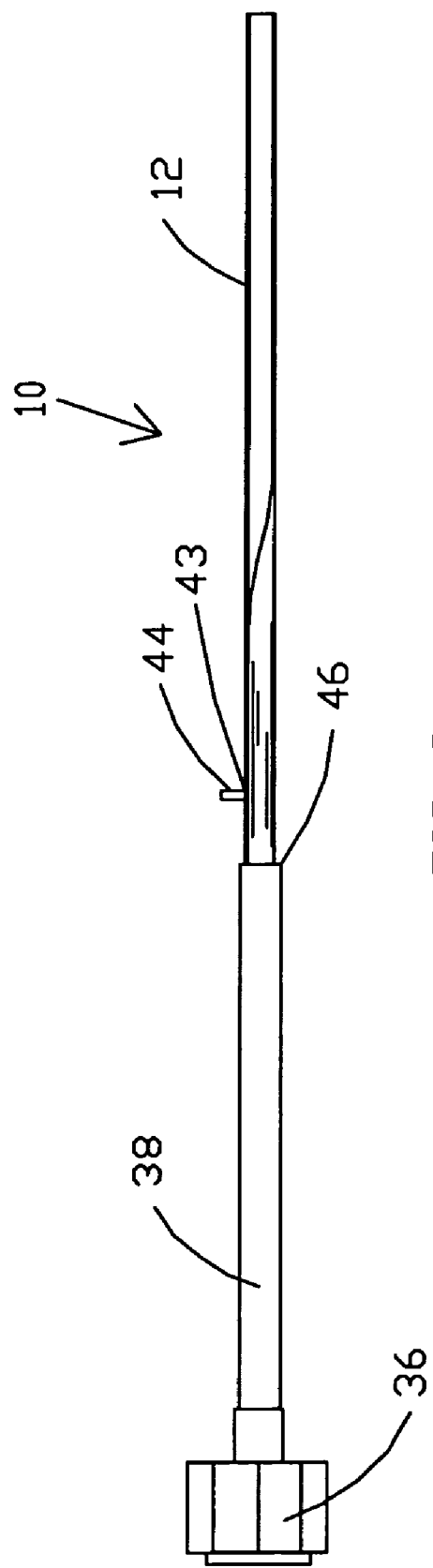

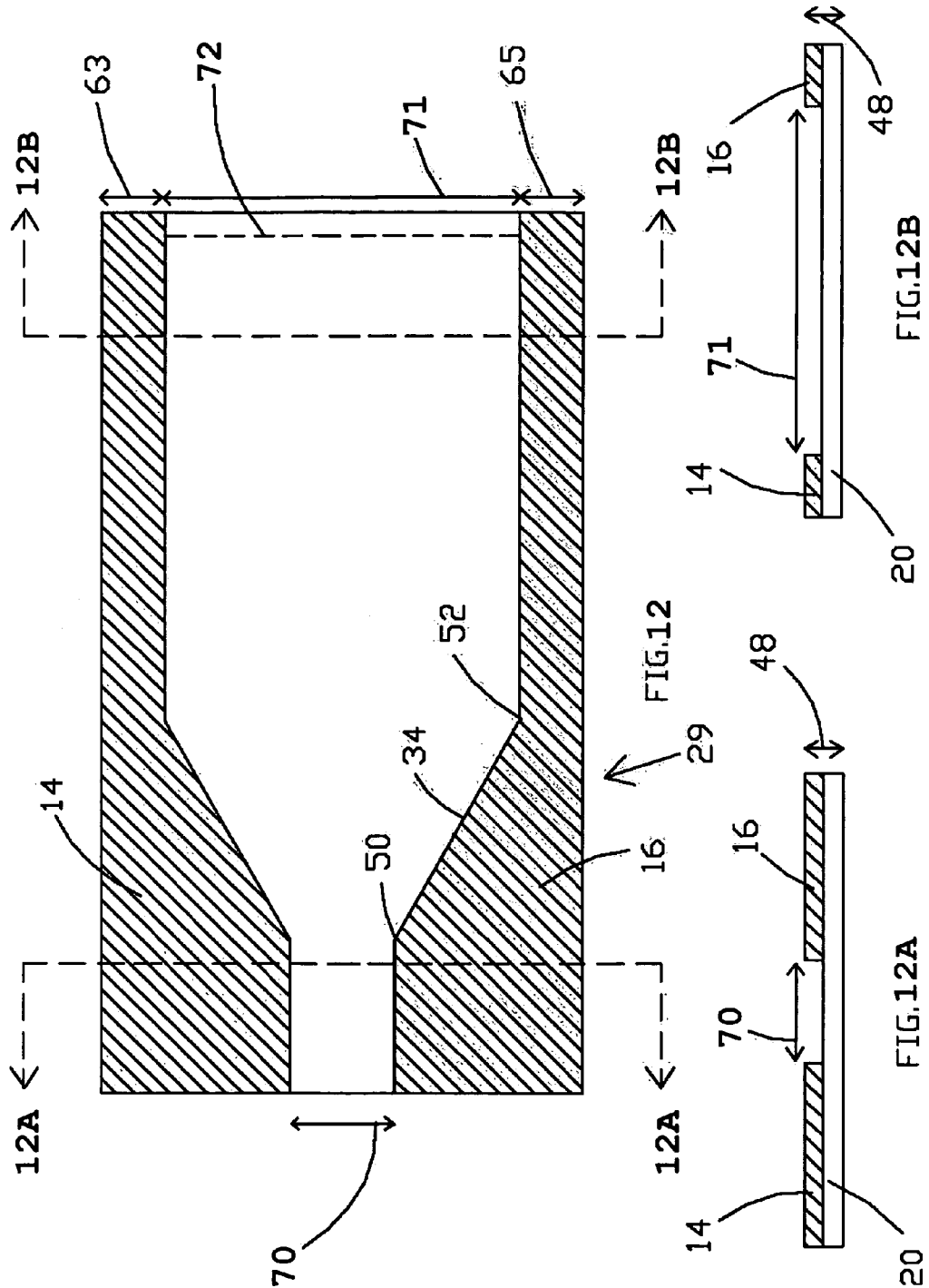

DIRECTIONAL MICROWAVE APPLICATOR AND METHODS

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 U.S.C. 2457).

BACKGROUND OF THE INVENTION

1. Field of the Invention

The present invention relates generally to microwave antennas and, more specifically, to a miniaturized directional microwave antenna for microwave therapy purposes that is highly suitable for use in catheters or syringes where limited space is available.

2. Description of Prior Art

Microwaves are utilized in various medical treatments. As one possible example, microwave ablation therapy may be utilized to treat damaged heart tissues or other tissues containing malignant or harmful cells. During microwave ablation treatments, the damaged tissue to be ablated may be located in one azimuthal direction with respect to the antenna whereas healthy tissue may be positioned in another azimuthal direction with respect to the antenna. It may often be desirable to ablate the damaged tissue by producing therein an increase in temperature while simultaneously limiting the increase in temperature in the healthy tissue.

Antenna directionality implies a focusing of energy. Higher antenna directionality or focusing generally requires a larger size antenna due to the need to provide antenna focusing elements or means. Non-limiting examples of focusing elements may comprise parasitic and/or active antenna elements, reflectors, directors, and the like. Within the small confines of a small diameter catheter or a syringe, there is seldom sufficient room for an aperture large enough to provide antenna directionality.

Several variations of monopole antennas have been used in the prior art for supplying RF or microwave frequency electromagnetic radiation in medical applications, often through the use of a catheter. These antennas typically have the property that radiation around the antenna (azimuthal radiation) is fairly symmetric. This can be disadvantageous in many instances, as discussed above, in which directionality is preferred in order to protect tissue on one side of the antenna while supplying energy to the opposite side.

In some prior art applications, a catheter-based antenna has been routed to an organ wherein sufficient interior space is available that permits expansion of the antenna. The antenna expands in order to increase the aperture size of the antenna, and hence, the directivity, e.g., Gu, Z., Rappaport, M., Wang, P. J., and VanderBrink, B. A., "Development and experimental verification of the wide-aperture catheter-based microwave cardiac ablation antenna", IEEE Trans. On Microwave Theory and Techniques, vol. 48, November 2000). Accordingly, these antennas are limited to use in special regions of the body.

The following patents disclose prior art efforts related to the above-described and/or other problems and studies:

U.S. Pat. No. 4,204,549, issued May 27, 1980, to Paglione discloses an apparatus for hyperthermia treatment that provides transmission of microwave energy for irradiation of tissues and simultaneous and concurrent and continuous measurement of the temperature of the heated tissues at the site of the treatment. The microwave energy is supplied to the site of treated tissue by a coaxial applicator, which is positioned near the tissue.

U.S. Pat. No. 4,311,154, issued Jan. 19, 1982, to Sterzer et al discloses an apparatus that uses microwave energy for the therapeutic and hyperthermic treatment of an internal body organ such as the prostate gland. An irregularly shaped coaxial applicator having a narrow portion and a wide portion is inserted through the male anus into the rectum such that a substantially maximum intensity of the microwave energy irradiates the prostrate gland for preferential heating of the prostate gland and a substantially minimum intensity irradiates untreated tissue. Temperature sensing means are positioned on the periphery of the applicator to measure the tissue environment irradiated by the microwave energy. A controller, operating with the temperature sensing means, is provided to maintain the temperature of the tissue environment within a desired temperature range.

U.S. Pat. No. 4,601,296, issued Jul. 22, 1986, to Yerushalmi, discloses an apparatus for hyperthermic treatment of tumors comprising a probe insertable into a body cavity in the vicinity of a tumor to be treated, the probe including a radiation emitting antenna and a conduit system for the passage of a cooling fluid adjacent the outer surface thereof for cooling of tissue lying adjacent the probe.

U.S. Pat. No. 4,776,086, issued Oct. 11, 1988, to Kasevich et al., discloses a microwave collinear antenna array applicator for for in situ or in vivo treatment of tumors and/or other materials by hyperthermia. The array consists of a plurality of harmonically related resonant coaxial antenna elements connected electrically in series to provide uniform heating along the entire length of the array. At the distal end of the array, a resistor may be provided at the inner conductor for steering the heating pattern. At the proximal end of the array, an impedance matching dielectric structure is provided to enable maximum power transfer to the array and to minimize stray leakage currents along the outside of the coaxial transmission line. The array may be made longer or shorter without changing frequency and therefore, depth of penetration by simply adding or subtracting half-wave resonant elements or sections of coaxial transmission line. A lossy sleeve member may be provided around the applicator to provide a localized source of heat.

U.S. Pat. No. 5,026,959, issued Jun. 25, 1991, to Ito et al., discloses an invention that relates to a microwave radiator for warming therapy inserted into a human body to cure focuses of the body such as tumors. It has a first and second high-frequency coaxial cable. The second high-frequency coaxial cable has an inner conductor and a plurality of ring conductors disposed at the outer periphery of the inner conductor via a dielectric. The second high-frequency coaxial cable is inserted into the focuses of the body, and warming therapy can be conducted using radiated electromagnetic waves.

U.S. Pat. No. 5,151,100, issued Sep. 29, 1992, to Abele et al., discloses a catheter device and method for heating tissue. The device has a catheter shaft constructed for insertion into a patient's body, and at least one chamber mounted on the catheter shaft. The catheter shaft has at least one lumen for fluid flow through the shaft. The chambers are defined by walls that are at least in part expandable. Fluid flows, through the lumens, between the chambers and a fluid source outside the body. The chambers can be filled with the fluid after they have been placed within the body. A heating device heats liquid within at least one of the chambers, so that heat is transmitted from the liquid to surrounding tissue by thermal conduction through the wall of the chamber. Means are provided for selectively directing heat transmission toward a selected portion of surrounding tissue. The chambers are fillable with fluid separately from each other, so that the chambers can occupy any of a plurality of possible total volumes. By selecting the total volume of chambers, compression of the tissue can be controlled, and hence the effectiveness of transfer of heat to the tissue can be controlled.

According to the method, the catheter device is used to heat tissue from within a duct in a patient's body. The chambers are inserted into the duct and filled with fluid. Liquid is heated within at least one of the chambers, and heat is selectively directed toward a selected portion of surrounding tissue.

U.S. Pat. No. 5,314,466, issued May 24, 1994, to Stern et al., discloses an assembly for steering and orienting a functional element at the distal end of a catheter tube that holds the functional element with its major axis aligned with the axis of the catheter tube for convenient steering to a tissue site. The mechanism can also pivot the functional element in response to an external force to orient the major axis of the functional element generally parallel to the plane of the tissue site, without bending the catheter tube.

U.S. Pat. No. 5,323,778, issued Jun. 28, 1994, to Kandarpa et al., discloses a method for imaging and heating body tissues with one probe, through use of a magnetic resonance imaging radio frequency source. The device may also be configured with a thermocouple to provide temperature-controlled heat therapy with sufficient image definition to control that therapy.

U.S. Pat. No. 5,370,644, issued Dec. 6, 1994, to Langberg, discloses a cardiac ablation apparatus including a solenoidal antenna, monitoring electrodes, and a coupling network at a distal end of a catheter transmission line, and another coupling network at the proximal end of the catheter transmission line to connect the catheter to the source of radiofrequency (RF) power and to an intracardiac electrogram monitor. Solenoidal antenna design includes single and multiple windings with varying geometrical features. Plated plastic tri-axial design of a transmission line offers unitary fabrication. A catheter with variable impedance electrode and gap coatings has features useful for both ablation and for hyperthermia applications.

U.S. Pat. No. 5,694,134, issued Dec. 2, 1997, to Barnes, relates to a phased array antenna for microwave and millimeter wave applications, using either microstrip line, coplanar waveguide, or other construction techniques incorporating a solid dielectric transmission line. A continuously variable phase delay structure which is used to control the beam pattern of the phased array antenna can be applied to the construction of resonant frequency tunable coplanar waveguide antennas and impedance tunable quarter-wave transformers. A thin film of barium strontium titanate or other nonlinear material is deposited upon the coplanar waveguide, and/or the patch antenna element. The dielectric constant of the thin film can be made to vary significantly by applying a DC voltage to the thin film. The propagation constant of a transmission line is directly proportional to the square root of the effective dielectric constant (assuming a lossless dielectric). In an array of multiple antenna elements provided with the feed structure using the disclosed transmission lines, the direction of the resultant main beam of the array can be made to vary over a complete half-sphere with only two adjustable DC voltages applied to the dielectric thin films.

U.S. Pat. No. 5,843,144, issued Dec. 1, 1998, to Rudie et al., discloses a method for treating an individual with diseased prostatic tissue, such as benign prostatic hyperplasia, includes inserting a catheter into a urethra to position a microwave antenna located within the catheter adjacent a prostatic region of the urethra. A microwave antenna is then driven within a power range for applying microwave energy substantially continuously to prostatic tissue to heat the prostatic tissue surrounding the microwave antenna at a temperature and for a time period sufficient to cause necrosis of the prostatic tissue.

U.S. Pat. No. 5,904,709, issued May 18, 1999, and other patents, to Arndt et al., disclose an exemplary method and apparatus for propagating microwave energy into heart tissues to produce a desired temperature profile therein at tissue depths sufficient for thermally ablating arrhythmogenic cardiac tissue to treat ventricular tachycardia and other arrhythmias while preventing excessive heating of surrounding tissues, organs, and blood. A wide bandwidth double-disk antenna is effective for this purpose over a bandwidth of about six gigahertz. A computer simulation provides initial screening capabilities for an antenna such as operating frequency, power level, and power application duration. The simulation also allows optimization of techniques for specific patients or conditions. In operation, microwave energy between about 1 gigahertz and about 12 gigahertz is applied to monopole microwave radiator having a surface wave limiter. A test setup provides physical testing of microwave radiators to determine the temperature profile created in actual heart tissue or ersatz heart tissue. Saline solution pumped over the heart tissue with a peristaltic pump simulates blood flow. Optical temperature sensors disposed at various tissue depths within the heart tissue detect the temperature profile without creating any electromagnetic interference. The method may be used to produce a desired temperature profile in other body tissues reachable by catheter such as tumors and the like.

U.S. Pat. No. 6,245,062, issued Jun. 12, 2001, to Berube et al., discloses a directional reflective shield assembly for a microwave ablation instrument having an antenna coupled to a transmission line. The antenna is formed to generate an electric field sufficiently strong to cause tissue ablation. The shield assembly includes a cradle device disposed about the antenna in a manner substantially shielding a surrounding area of the antenna from the electric field radially generated therefrom. The cradle device further provides a window portion communicating with the antenna which is strategically located relative the antenna to direct a majority of the field generally in a predetermined direction.

U.S. Pat. No. 6,289,249, issued Sep. 11, 2001, and other patents, to Arndt et al., disclose an exemplary method, simulation, and apparatus that are highly suitable for treatment of benign prostatic hyperplasia (BPH). A catheter is disclosed that includes a small diameter disk loaded monopole antenna surrounded by fusion material having a high heat of fusion and a melting point preferably at or near body temperature. Microwaves from the antenna heat prostatic tissue to promote necrosing of the prostatic tissue that relieves the pressure of the prostatic tissue against the urethra as the body reabsorbs the necrosed or dead tissue. The fusion material keeps the urethra cool by means of the heat of fusion of the fusion material. This prevents damage to the urethra while the prostatic tissue is necrosed. A computer simulation is provided that can be used to predict the resulting temperature profile produced in the prostatic tissue. By changing the various control features of the catheter and method of applying microwave energy a temperature profile can be predicted and produced that is similar to the temperature profile desired for the particular patient.

U.S. Pat. No. 6,383,182, issued May 7, 2002, to Berube et al., discloses a directional ablation instrument for ablation of a targeted tissue. The instrument includes a transmission line having a proximal portion suitable for connection to an electromagnetic energy source, and an elongated antenna device having a longitudinal axis and an end coupled to the transmission line. The antenna is adapted to generate an electric field sufficiently strong to cause tissue ablation of the targeted tissue. An elongated support assembly includes a central axis, and an ablation surface extending longitudinally along an exterior surface portion of the support assembly. The support assembly is configured to receive the antenna device in the ablation surface such that the longitudinal axis of the antenna device is off-set from the support assembly central axis. Further, the antenna device is oriented toward the surface portion for positioning of the antenna device substantially adjacent to or in contact with the targeted tissue during operable use.

U.S. Pat. No. 6,527,768, issued Mar. 4, 2003, to Berube discloses a microwave ablation instrument including a transmission line having a first conductor and a second conductor suitable for the transmission of microwave energy. A horn antenna device is mounted to the end of the transmission line, and include an outer conductor and an inner conductor. The outer conductor of the horn antenna is electrically coupled to the second conductor of the transmission line, and includes a peripherally extending interior wall flaring outwardly to define a recess therein. The inner conductor of the horn antenna is electrically coupled to the first conductor of the transmission line and terminates in the outer conductor recess. The inner conductor and the outer conductor cooperate to emit an electromagnetic field sufficiently strong to cause tissue ablation in a direction generally away from the flared interior wall of the outer conductor.

U.S. Pat. No. 6,496,736, issued Dec. 17, 2002, to Carl et al., discloses an exemplary method and apparatus to treat atherosclerosis wherein the artery is partially closed by dilating the artery while preserving the vital and sensitive endothelial layer thereof. Microwave energy having a frequency from 3 GHz to 300 GHz may be propagated into the arterial wall to produce a desired temperature profile therein at tissue depths sufficient for thermally necrosing connective tissue and softening fatty and waxy plaque while limiting heating of surrounding tissues including the endothelial layer and/or other healthy tissue, organs, and blood. The heating period for raising the temperature a potentially desired amount, about 20 degrees Centigrade, within the atherosclerotic lesion may be less than about one second. In one embodiment of the invention, a radically beveled waveguide antenna is used to deliver microwave energy at frequencies from 25 GHz or 30 GHz to about 300 GHz and is focused towards a particular radial sector of the artery. Because the atherosclerotic lesions are often asymmetrically disposed, directable or focused heating preserves healthy sectors or the artery and applies energy to the asymmetrically positioned lesion faster than a non-directed bean. A computer simulation predicts isothermic temperature profiles for the given conditions and may be used in selecting power, pulse duration, beam width, and frequency of operation to maximize energy deposition and control heat rise within the atherosclerotic lesion without harming healthy tissues or the sensitive endothelium cells U.S. Pat. No. 6,690,963, issued Feb. 10, 2004, to Ben-Haim et al., discloses a locating system for determining the location and orientation of an invasive medical instrument, for example a catheter or endoscope, relative to a reference frame, comprising: a plurality of field generators which generate known, distinguishable fields, preferably continuous AC magnetic fields, in response to drive signals; a plurality of sensors situated in the invasive medical instrument proximate the distal end thereof which generate sensor signals in response to said fields; and a signal processor which has an input for a plurality of signals corresponding to said drive signals and said sensor signals and which produces the three location coordinates and three orientation coordinates of a point on the invasive medical instrument.

U.S. Patent Application Publication No. 2002/0128642, published Sep. 12, 2002, and other publications, to Berube et al., discloses a directional ablation instrument for ablation of a targeted tissue. The instrument includes a transmission line having a proximal portion suitable for connection to an electromagnetic energy source, and an elongated antenna device having a longitudinal axis and an end coupled to the transmission line. The antenna is adapted to generate an electric field sufficiently strong to cause tissue ablation of the targeted tissue. An elongated support assembly includes a central axis, and an ablation surface extending longitudinally along an exterior surface portion of the support assembly. The support assembly is configured to receive the antenna device in the ablation surface such that the longitudinal axis of the antenna device is offset from the support assembly central axis. Further, the antenna device is oriented toward the surface portion for positioning of the antenna device substantially adjacent to or in contact with the targeted tissue during operable use.

Books with related subject matter may include the following:

"Microstrip Lines and Slotlines," 1996, K. C. Bupta et al., published by Artech House, in Norwood Mass., in Chapter 7.

"Design of Nonplanar Microstrip Antennas and Transmission Lines," 1999, by K. L. Wong et al, published by John Wiley & Sons, Inc., New York, N.Y., in Chapter 8.

It would be desirable to provide an antenna that can be made sufficiently small to function as a catheter or syringe antenna and to provide directionality for radiating, with azimuthal directionality, into a biological medium wherein space is not otherwise available. Those skilled in the art have long sought and will appreciate the present invention that addresses these and other problems.

SUMMARY OF THE INVENTION

An object of the present invention is to provide an improved apparatus and method for miniature microwave antennas.

Yet another objective of the present invention is to provide a miniaturized directional microwave antenna.

Any listed objects, features, and advantages are not intended to limit the invention or claims in any conceivable manner but are intended merely to be informative of some of the objects, features, and advantages of the present invention. In fact, these and yet other objects, features, and advantages of the present invention will become apparent from the drawings, the descriptions given herein, and the appended claims.

Accordingly, the present invention provides a microwave or radiowave apparatus which may comprise one or more elements such as, for example, an elongate structure, a substantially non-radiating portion of the elongate structure with a waveguide (or transmission line) mounted on or closely adjacent to the surface of the elongate structure. The waveguide defines at least one waveguide gap therebetween.

Other elements may comprise a radiating portion of the elongate structure comprising an antenna conductor and one or more antenna elements defining an antenna gap therebetween which is continuous with the waveguide gap. The waveguide gap width is smaller than the antenna gap width.

The antenna elements may preferably be smaller in width as compared to the waveguide conductors. The antenna conductor and the one or more antenna elements are preferably mounted on or closely adjacent to the surface of the elongate structure. In one preferred embodiment, the outer surface of the elongate structure may be rounded.

In one preferred embodiment, the waveguide conductors and the one or more antenna elements comprise substantially continuous second and third ground conductors which extend along the substantially non-radiating portion and the radiating portion. The second and third conductors may be electrically shorted to each other to effectively provide a single conductor.

An impedance matching section may be provided between the substantially non-radiation portion and the radiating portion. The respective widths of the ground conductors may preferably smoothly vary within the impedance matching section. The gap widths defined therein may also preferably smoothly vary. This compares with the waveguide gap width in the non-radiating portion which may preferably be constant. The elongate structure may comprise substantially non-conductive material in both the non-radiating portion and the radiating portion. The microwave apparatus may further comprise substantially non-conductive surface material wherein the waveguide conductors may be mounted on or within the non-conductive surface material. In one embodiment, the center waveguide conductor and the antenna conductor comprise a first continuous conductor which extends continuously and coaxially along the non-conductive material from the non-radiating portion to the radiating portion.

The microwave apparatus may further comprise a coaxial cable and an electrical connection between the substantially non-radiating portion and the coaxial cable. The coaxial cable may comprise a sheath and an inner conductor. The sheath may be electrically connected to the ground conductors and the inner conductor may be electrically connected to the center waveguide conductor. In one example, the inner conductor is shorted to the center waveguide conductor. In another example, the inner connector is electromagnetically coupled to the first waveguide conductor.

In one preferred embodiment, the non-radiating portion and the radiating portions comprise substantially equal diameters. As one example, the substantially equal diameters are less than about 0.1 inch. The microwave apparatus may further comprise a non-conductive outermost covering, such as heat shrink or any other suitable material.

The first antenna conductor of the radiating portion is preferably spaced sufficiently far enough from the ground conductors to act either as a RF/microwave radiator or as a lossy waveguide or both. The ground conductors may be substantially arc-shaped when viewed in cross-section and cause the first antenna conductor to radiate microwave energy predominately in an azimuthal direction with respect to the first antenna conductor.

In another embodiment, the present invention may comprise a microwave waveguide portion with a curved first outer surface or layer comprised of non-conductive material. A plurality of waveguide conductors may then be disposed on the curved first outer surface or layer and may define one or more gaps therebetween to provide a microwave waveguide or transmission line.

A microwave radiating portion is electrically connected to receive microwave energy from the microwave waveguide portion. The microwave radiating section may comprise one or more radiating conductors disposed on the curved surface of the non-conductive material for radiating substantially all of the microwave energy received from the microwave waveguide portion.

The present invention may further comprise a method for determining dimensions for a generally cylindrical waveguide. The method may comprise steps such as selecting a desired characteristic impedance, determining an effective dielectric constant for layers radially outwardly and radially inwardly of the center conductor, and determining an approximate gap width between the center conductors and the one or more ground conductors which will produce the desired characteristic impedance. In one embodiment, the outermost layer of material may comprise the biological material. The method may further comprise plotting gap width with respect to impedance.

In yet another embodiment, the invention may comprise a transmission line portion, a radiating portion electrically connected to receive energy from the transmission line portion, a curved waveguide non-conductive surface, and an interior passageway extending through the microwave waveguide portion and the microwave waveguide portion. The interior passageway may be filled with air or, if desired, any other suitable materials including fluids, such as cooling fluids.

While the present invention will be described in connection with presently preferred embodiments, it will be understood that it is not intended to limit the invention to those embodiments. On the contrary, it is intended to cover all alternatives, modifications, and equivalents included within the spirit of the invention and as defined in the appended claims.

BRIEF DESCRIPTION OF THE DRAWINGS

FIG. 1 is an elevational view of a microwave applicator with a waveguide section and an antenna section in accord with possible embodiments of the present invention;

FIG. 1A is a cross-sectional view along lines 1A-1A of FIG. 1 showing in greater detail elements of a waveguide section in accord with possible embodiments of the present invention;

FIG. 1B is a cross-sectional view along lines 1B-1B of FIG. 1 showing in greater detail elements of an antenna section in accord with possible embodiments of the present invention;

FIG. 2 is an elevational view, partially in phantom lines, showing a coupling between a coaxial cable (before trimming the length of the coaxial cable center conductor, shown bent at a 90 degree angle) and a waveguide section in accord with possible embodiments of the present invention;

FIG. 3 is an elevational view showing an interconnected coaxial cable and microwave applicator as shown in FIG. 1 (before trimming the length of the coaxial cable center conductor) and a waveguide section in accord with possible embodiments of the present invention;

FIG. 6A is a cross-sectional view along lines 6A-6A of FIG. 6 showing in greater detail elements of the modified coplanar waveguide of FIG. 6 which if rolled would become a waveguide section of FIG. 1 in accord with possible embodiments of the present invention;

FIG. 6B cross-sectional view along lines 6B-6B of FIG. 6 showing in greater detail elements of the modified coplanar waveguide of FIG. 6 which if rolled would become an antenna section of FIG. 1 in accord with possible embodiments of the present invention;

FIG. 12 is another elevational view of a modified flexible coplanar waveguide which may be rolled for making a prototypic version of the waveguide section and antenna section of a microwave applicator in accord with possible embodiments of the present invention;

FIG. 12A is a cross-sectional view along lines 12A-12A of FIG. 12 showing in greater detail elements of the modified coplanar waveguide of FIG. 12 which if rolled would become a waveguide section in accord with possible embodiments of the present invention;

FIG. 12B cross-sectional view along lines 12B-12B of FIG. 12 showing in greater detail elements of the modified coplanar waveguide of FIG. 12 which if rolled would become an antenna section in accord with possible embodiments of the present invention.

BRIEF DESCRIPTION OF PREFERRED EMBODIMENTS

Figure 4:
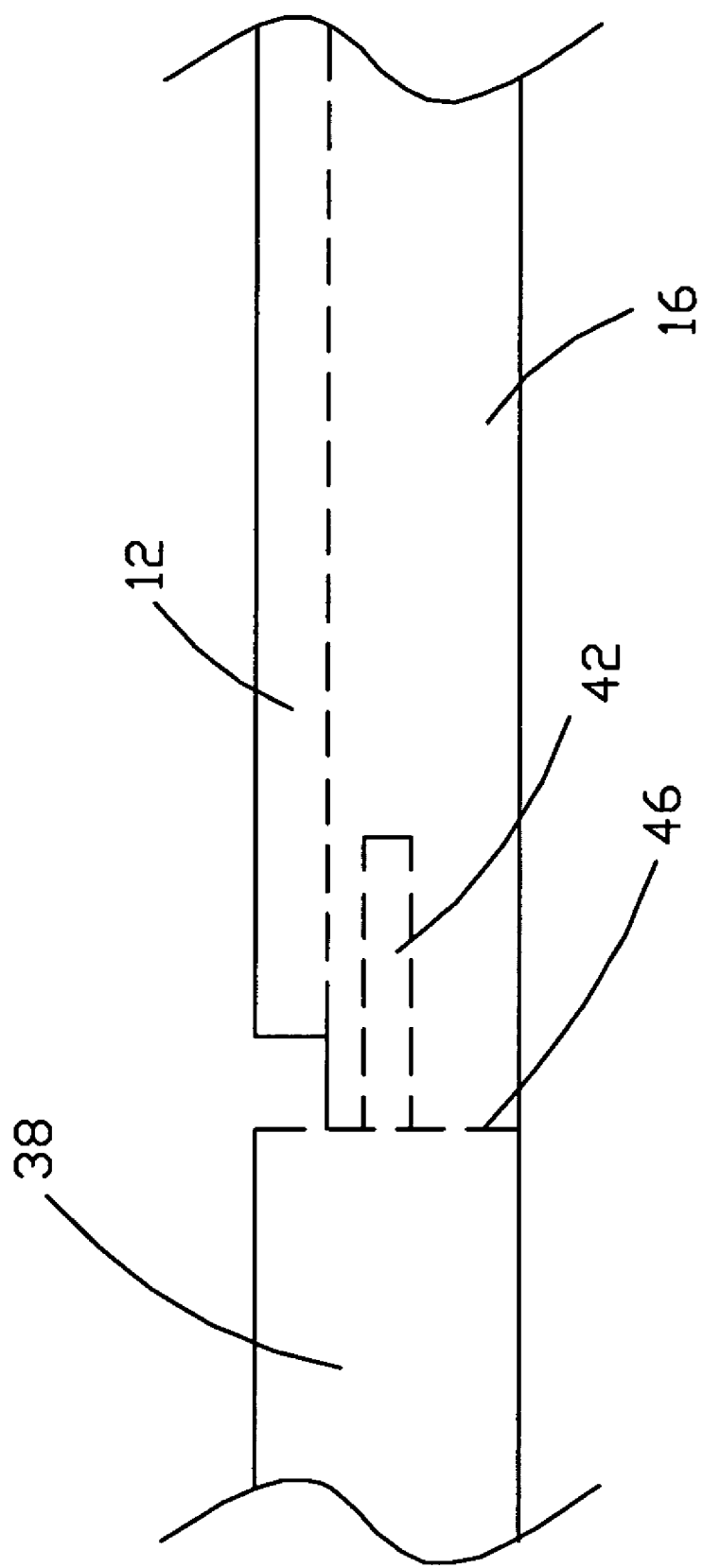
FIG. 4 is an elevational view, partially in phantom lines, showing an electromagnetic coupling between a coaxial cable center conductor and a waveguide section in accord with possible embodiments of the present invention.

A miniature directional microwave antenna in accord with the present invention has various medical applications such as, but not limited to, a microwave angioplasty system, a microwave-based hyperthermia treatment system to replace or supplement vertebroplasty, a microwave treatment system for prostate tumors where need for directional heating is required within small confines, and/or for use in biological sterilization applications. Because of the small diameter, circumference, or periphery, the present invention may also be used as a catheter, syringe, and/or cannula antenna. The present invention may also be used for sterilization in regions that would otherwise be difficult to access. Terms such as catheter, syringe, and cannula, or any other means for insertion into tissue, may be utilized herein interchangeably.

Referring now to the drawings, and more specifically to FIG. 1, FIG. 1A and FIG. 1B, there is shown an embodiment of a microwave applicator 10 in accord with the present invention. Microwave applicator 10 comprises transmission line or waveguide section 24 and radiating or antenna section 26.

In one possible embodiment of the present invention, a directional microwave antenna for antenna section 26 is based on what may be referred to herein as the concept of an open-ended cylindrical coplanar waveguide (CCPW) that acts both as a transmission line and as a radiating element. While the cross-sections and present mathematical models of the microwave applicator 10, as suggested in FIG. 1A, FIG. 1B, and FIG. 9 utilize a generally circular cross-section or circular cross-sectional layers or elements, the invention is not limited to purely circular cross-sectional designs. For instance, the waveguide and/or antenna portions of the present invention may have generally circular, elliptical, or other generally rounded or curved cross-sectional shapes, if desired. Furthermore, as discussed hereinafter, the cross-sectional shape may be varied or selected depending on a desired shape of the catheter, syringe, or cannula for insertion of the microwave applicator into the body and/or to affect the depth of penetration, the azimuthal radiation angle, the focus point of the antenna, and/or for other considerations, as deemed desirable.

In general concept of operation of microwave applicator 10, radiating section 26 of the microwave applicator 10 may be formed by increasing the microwave gap width 56 (see FIG. 1A) such as by decreasing the size of ground conductor sections 14 and 16 (see difference in size of sections 14 and 16 between FIG. 1A and FIG. 1B). With ground conductor sections 14 and 16 closely spaced to center strip 12 as shown in FIG. 1A, microwave applicator 10 operates as a transmission line or a waveguide to thereby provide waveguide section 24 of microwave applicator 10. With ground conductors 14 and 16 distantly spaced from center strip 12 as indicated in FIG. 1B, microwave applicator 10 operates as an antenna whereby the increased spacing results in radiation into and/or absorption by the surrounding medium thereby provide antenna section 26 of microwave applicator 10.

The decrease in size of ground conductor sections 14 and 16 permits an increase in the size of the gap between the center strip 12 and corresponding ground conductor sections 14 and 16. With smaller gap 56, the combination of center strip 12 and conductor sections 14 and 16 act as a waveguide or transmission line. With a larger gap between center strip 12 and conductor sections 14 and 16, as shown in FIG. 1B, the traveling wave is more loosely coupled between the center strip 12 and the ground conductor sections 14 and 16 thereby allowing the electromagnetic field to extend further from the applicator, either radiating from the antenna/applicator or becoming absorbed by the surrounding medium in an azimuthal direction with respect to center strip 12. Thus, as shown in FIG. 1, FIG. 1B, (and also FIG. 6B), the gap width between ground conductor sections 14 and 16 and center strip 12 is increased to thereby alter the function of this section to that of an antenna. Accordingly, the radiation from the antenna section 26 may be directed by abbreviated ground conductors 14 and 16, thereby allowing a user to heat targeted tissue without damaging the surrounding healthy tissue. As discussed below, microwave applicator 10 may be operated as a resonant device or as a traveling wave device.

One necessary aspect of the present invention is that of determining the physical dimensions of transmission line section 24 and radiating element section 26 so that most of the applied power is radiated into the surrounding tissue. The process of determining the most suitable dimensions includes developing a predictive mathematical model for this purpose, with associated variables as suggested by FIG. 9, which is discussed hereinafter. In one preferred embodiment, it has been found that a catheter in accord with the present invention spatially directs about 97.75% of its input power into an artificial human tissue sample.

Cylindrical coplanar waveguides and/or other miniaturized waveguide and/or antenna elements as shown herein are not commercially available and therefore require novel fabricating techniques. In one possible method of the invention for making microwave applicator 10 a coplanar waveguide circuit such as coplanar waveguide 29 (see FIG. 6) is etched onto a piece of flexible circuit board to thereby provide layer 20 and conductors 12, 14, 16 (see FIG. 6A and FIG. 6B). In one example, the flexible circuit board may be 5 mil (0.005 inch) thick as indicated at 48 in FIG. 6A and FIG. 6B. (Note that the drawings are not to scale and shown in a manner selected for ease of viewing the various components). The circuit board may then be wrapped around a piece of non-conductive Teflon tubing 22 or other suitable materials as indicated in see FIG. 1A and FIG. 1B.

Figure 6:
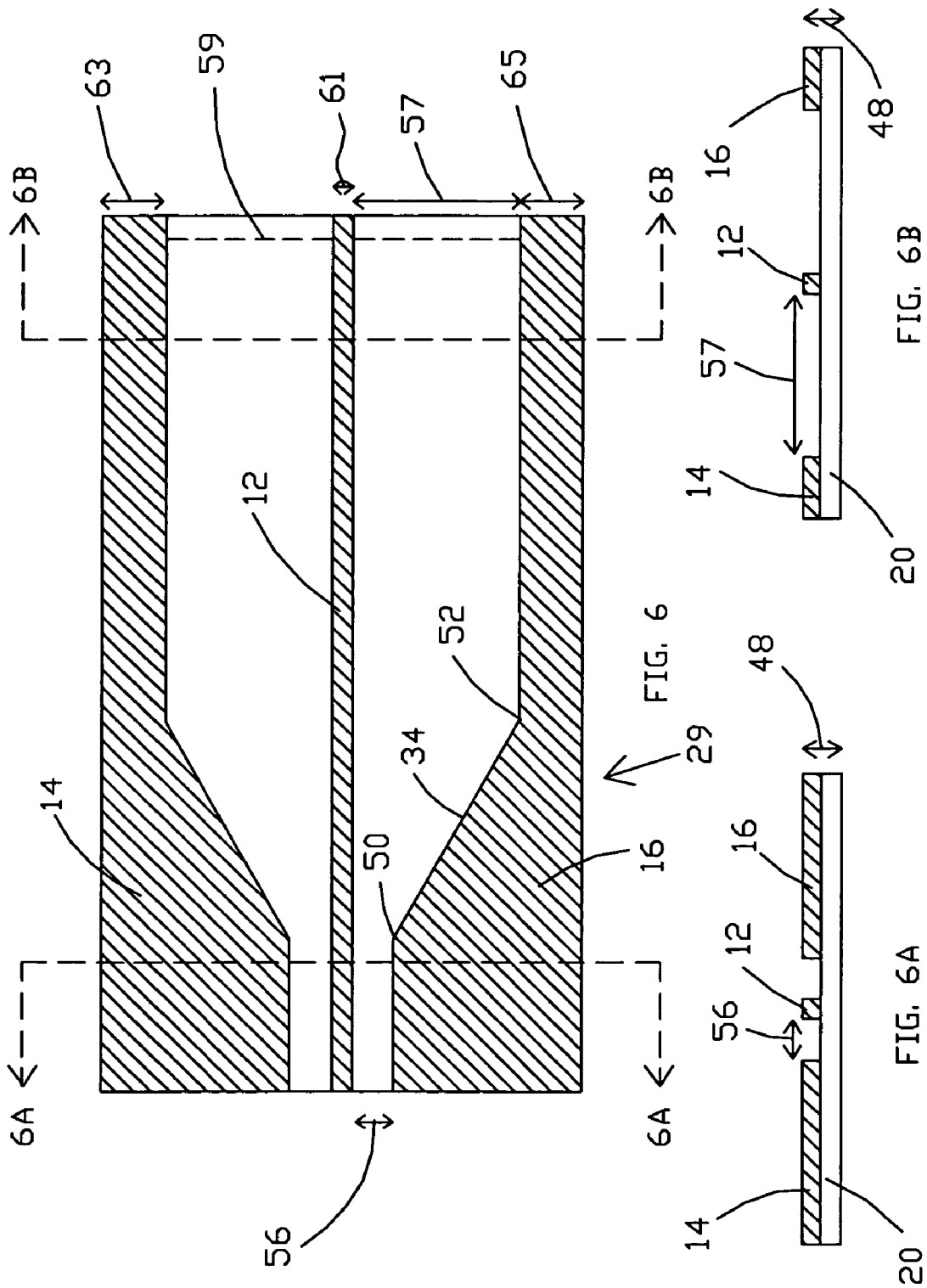
FIG. 6 is an elevational view of a modified flexible coplanar waveguide which may be rolled for making a prototypic version of the waveguide section and antenna section of the microwave applicator of FIG. 1 in accord with possible embodiments of the present invention.

In FIG. 6, a modified coplanar waveguide circuit 29 is shown from a top view prior to being wrapped around Teflon tubing 22 (see FIG. 1A) or possibly other non-conductive materials. FIG. 6A and FIG. 6B show cross-sections of the circuit board prior to the flexible circuit board being wrapped around the Teflon tubing. Note that dimensions of the figures are not intended to be to scale and are selected mainly for ease of viewing the various components.

One significant advantage of the construction is that because conductors are positioned along or near the periphery of preferably non-conductive circuit board material 20, the inner portion, such as that shown at 30 and 32 of the microwave applicator 10 is left available for any desired suitable function. For instance, depending on the particular construction, the inner region might be used for cooling fluid, if desired. For instance, where blood flow is not available for cooling purposes, e.g., for use in the urethra for prostate treatment purposes, then cooling fluid could be introduced through an otherwise unused central region. Note that the central region could be segmented so that a cooling fluid passageway could be positioned further or closer to center strip 12, as desired. Different salinity fluids, temperatures and so forth could also be utilized in different portions of the central region of 30 and 32 and or larger regions as discussed hereinafter which may depend on construction techniques. As well, the existence of the central region in this very small embodiment (e.g. less than 0.1 inches maximum diameter) provides for quite significant reductions in diameter where fluids, other interior devices, or other interior structures are not utilized.

While prototypes have been made by starting with modified coplanar waveguide 29 shown in FIG. 6, and wrapping that around Teflon material 22, it is to be understood that other manufacturing techniques may be utilized. For instance, a cylindrical metal plated insulator, similar to that of the circuit board 29 prior to etching of conductors 12, 14, and 16, might be the starting point. The desired pattern of conductors 12, 14, and 16 could then be etched. In this way, Teflon material 22 is not necessary and it is not necessary to provide the solder joint or solder joint seam indicated in FIG. 1A and FIG. 1B. An electrically insulative cylindrical member or elliptical cross-sectional elongate member could be utilized as the starting point and metallic conductors 12, 14, and 16 could be sprayed or painted thereon in the desired pattern. The electrically insulative elongate member could be at least semiflexible or have a flexible portion to avoid the need for a coaxial cable connection that is part of the inserted catheter. Moreover, the internal components or lack thereof could be quite different with this construction. If desired to make microwave applicator smaller, various construction techniques, some of which are discussed herein, would permit significant reductions in size. Thus, the present inventive method is not limited to rolling a circuit board for creation of microwave applicator 10.

As noted above, in one embodiment of the invention the edges of circuit 29 (see FIG. 6) are soldered together to form a cylinder as indicated by the solder joint in FIG. 1A and FIG. 1B. Adapter 40 (see FIG. 2) may then be used to connect the resulting microwave applicator 10 to a radio frequency (RF) source using a standard coaxial cable connector such as coupling 36. In one preferred embodiment, adapter 40 is a semi-rigid coaxial cable 38 with SMA male connector 36 on one end. Extruded Teflon or other internal coaxial non-conductive material is made available, such as by removing the coaxial sheath, on the opposite end as indicated in FIG. 2. In one possible embodiment, center conductor 42 of semi-rigid cable 38 is bent to extend as indicated by extension 44. After or before connection with microwave applicator 10, as shown in FIG. 3, extension 44 may be preferably trimmed so that it is slightly exposed outside the extruded Teflon at the approximate diameter of microwave applicator 10.

The complete antenna or catheter assembly, shown in FIG. 3, is formed by sliding the microwave applicator 10 over the extruded Teflon section of the adapter (see FIG. 2) and soldering it in place. As suggested in FIG. 3, the catheter ground path may be completed by soldering ground conductors 14 and 16 to the outer conductor, generally the coaxial sheath, of adapter 40 as indicated at 46 such that conductors 14 and 16 are electrically shorted together and electrically shorted to the coaxial cable sheath. The signal path is completed by soldering center conductor extension 44 of adapter 40 to the center strip 12 of microwave applicator 10 such that center conductor 42 and center strip 12 are electrically shorted together. Extension 44 is then preferably trimmed to the diameter of microwave applicator 10 and may be smoothed by sanding, grinding, or other suitable means. Once the catheter is completely assembled, a piece of heat shrink tubing (not shown) encapsulates the entire circuit to protect it and to prevent the circuit from making contact with the surrounding tissue.

Other electrically insulative materials may also be utilized for covering the catheter including specialized materials suitable for catheters. In some methods of building, mentioned hereinbefore and discussed again hereinafter, the electrically insulative outermost material may already be present so that no heat shrink or other coating material is required or desired.

FIG. 3 shows direct solder connection 43 between center conductor 42 of the adapter 40 and the center strip 12 of microwave applicator 10 prior to removing the excess of extension 44 which extends beyond the outer surface of microwave applicator 10. One possible alternate method of connecting adapter 40 to microwave applicator 10 is through electromagnetic coupling. One conceptual means for this is shown in FIG. 4. The advantage of the electromagnetic coupling connection method shown in FIG. 4 is that the center conductor solder joint 43 (see FIG. 3) is not required. This simplifies the construction of the completed catheter and smoothes the outer profile of the catheter. As discussed earlier, if adapter 40 is not necessary to form part of the overall catheter, as may occur without a rolled construction method, then other types of connections become available that are not particularly of concern as far as the outer profile of the resulting catheter.

Figure 5:
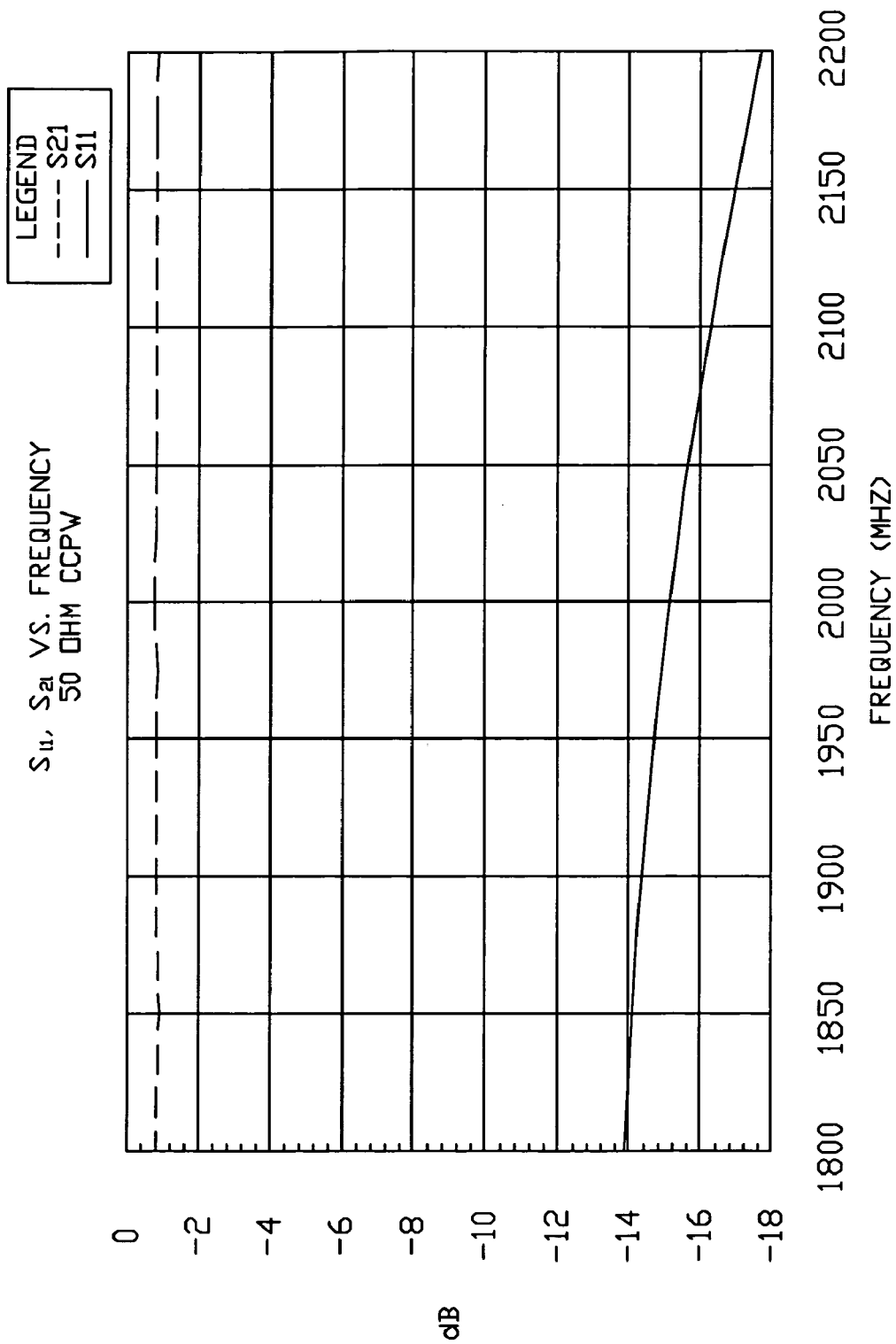
FIG. 5 is a chart which shows excellent transmission characteristics of the system of the non-radiating part of FIG. 3 wherein the well matched waveguide or transmission line section provides a low-loss link between two coaxial cables in accord with possible embodiments of the present invention.

Suitable equations for characterizing waveguide 24 were obtained by applying existing equations for a multi-layer flat coplanar waveguide in conjunction with existing equations for a single-layer cylindrical coplanar waveguide. For instance, equations for multilayer coplanar waveguide are provided by K. C. Bupta et al, entitled "Microstrip Lines and Slotlines," published by Artech House, in Norwood Mass., in 1996, Chapter 7. Equations for single-layer cylindrical coplanar waveguides are provided, for instance, by K. L. Wong et al, entitled "Design of Nonplanar Microstrip Antennas and Transmission Lines," published by John Wiley & Sons, Inc., New York, N.Y., in 1999, Chapter 8. A mathematical model based on the above equation but which describes characteristics of the unique construction of microwave applicator 10 is discussed hereinafter in conjunction with FIG. 9. To test the mathematical model for the cylindrical coplanar waveguide, an initial design for a 50-Ohm transmission line on a cylindrical structure, covered with a dielectric paste (relative permittivity 10.2) and based on the mathematical model, was constructed. The dielectric paste was used as a superstrate with high contrast relative to the base dielectric so that any effects of the superstrate could be tested. Dimensional details of the transmission line are discussed hereinafter. Reflection and transmission test results from the small section of 50-Ohm transmission line are shown in FIG. 5. The plot in FIG. 5 shows that excellent impedance match and transmission characteristics were obtained for the microwave transmission line with a high dielectric superstrate. The same math model, with the permittivity for the dielectric paste replaced by that for shrink tubing, was used to design the waveguide section (FIG. 1A) that connects the coaxial transmission line to the antenna section (FIG. 1B). of the catheter.

Radiating or antenna section 26 shown in FIG. 1, as discussed hereinbefore, is preferably an open-ended section as indicated by modified coplanar waveguide circuit 29 shown in FIG. 6. As indicated in FIG. 6, the circuit is modified so that ground conductors 14 and 16 are tapered away from center strip 12. The increased gaps between the center conductor and the ground conductors 14 and 16 result in an increase in radiation over the antenna section. The radiation from the gap is directed due to the ground conductors 14 and 16 reflecting power upward and away from the ground conductors 14 and 16. This radiation mechanism stands in contrast to that of the monopole antenna, which would typically radiate power symmetrically in azimuthal angles around the transmission line axis. As shown in FIG. 1B, ground conductors 14 and 16 may preferably have an arc-shaped cross-section. Note that ground conductors 14 and 16 are preferably electrically shorted together to effectively provide a single ground conductor. Further, the resulting width of combined ground conductors 14 and 16 as compared to the width of center conductor 12 is also a relevant consideration for controlling the amount of directivity. For instance, if the width of center conductor 12 and the combined widths of ground conductors 14 and 16 are equal, then directionality will be reduced and may be of little practical effect. As indicated in FIG. 6, in one preferred embodiment discussed hereinafter, width 61 of center conductor 12 is approximately 10 mils and the combined widths 63 and 65 of ground conductors 14 and 16 (prior to be rolled as indicated in FIG. 6) is approximately 60 mils. As used herein ground conductors may refer to being connected to sheath of a coaxial cable, or being connected to a common connection, or being connected to any known reference, or may simply be a label for conductors positioned to act as reflectors or parasitic elements for enabling directional radiation of microwaves.

FIG. 1, FIG. 1A, and FIG. 1B all show how the ground section, i.e., conductors 14 and 16, of microwave applicator 12 is tapered at taper section 34 so that that the ground section, or conductor 16 as seen from the elevational view of FIG. 1, resides below top or center conductor element 12. The combined width of 14 and 16 is preferably greater than the width of element 12 in order to create a preferred direction of radiation above element 12.

As discussed earlier, FIG. 6 shows coplanar circuit 29 before it is wrapped around Teflon tubing 22 as per one possible embodiment of the invention. FIG. 6 may also be utilized to more easily show presently preferred dimensions of both transmission line or waveguide section 24 and radiating element or antenna section 26 for microwave applicator 10.

As shown in FIG. 6, gap width W, as indicated by 56, is varied gradually from about 20 mils beginning at 50 to a gap width of about 70 mils at 52 so there is no step-change in the geometry of the line. Thus, width 57 is about 70 mils. Taper 34 may be angled with corners at 50 and 52 or may be smoothed or curved as desired. This tapered design reduces impedance mismatches between the junction of transmission line or waveguide section 24 and radiating element or antenna 26. Thus, in a preferred embodiment taper 34 comprises a taper junction or impedance matching section between transmission line or waveguide section 24 and antenna 26.

The center strip 12 width S may preferably be held constant at 10 mils, the same width that was used for center strip 12 of 50-Ohm transmission line or waveguide section 24. Thus, the antenna element is preferably an extension of center strip 12, just as the ground plane conductors in antenna section 26 are extensions of ground plane conductors 14 and 16. The length of the center strip was optimized through laboratory tests for maximum power transfer as described in the following section. The width of ground conductors 14 and 16, for this embodiment, varies from about 100 mils to about 30 mils. However, the dimensions of ground plane conductors 14 and 16 may change depending on the circumference of microwave applicator 10.

The length of the radiating section (FIG. 6B) is designed to optimize the power transferred to the media surrounding the antenna. This is accomplished by one of two methods. The first method is to design the length of the radiating section so that the antenna is resonant in the relevant environment. Although there are an infinite number of resonances, it is recognized that in the two preferred embodiments, the length is equal to either one-quarter or one-half of an effective wavelength, where the effective wavelength refers to the wavelength in the relevant environment. The relevant environment is determined by the materials and design of the antenna as well as the surrounding media. In the case in which the length is equal to one-quarter of an effective wavelength, the top conductor 12 is shorted to the ground conductors 14 and 16 at the end of the antenna section as indicated in dash by shorting wire or shunt 59 in FIG. 6 which may be manufactured into the design prior to rolling or added subsequently. The use of the one-quarter effective wavelength permits for a shortened antenna length where this is desirable. In the second method for optimizing power transfer to the surrounding media, the radiating section is designed to function as a traveling wave antenna as opposed to a resonant antenna. The power in the wave is dissipated by radiation into, and absorption by, the surrounding media as the wave propagates along the antenna section. When the wave reaches the open or shorted end of the antenna section, the remaining power is reflected and then travels toward the waveguide section (FIG. 6A). In the preferred embodiment of this method, the length is such that most or all of the power has been dissipated before the reflected wave reaches the waveguide section.

Figure 7:
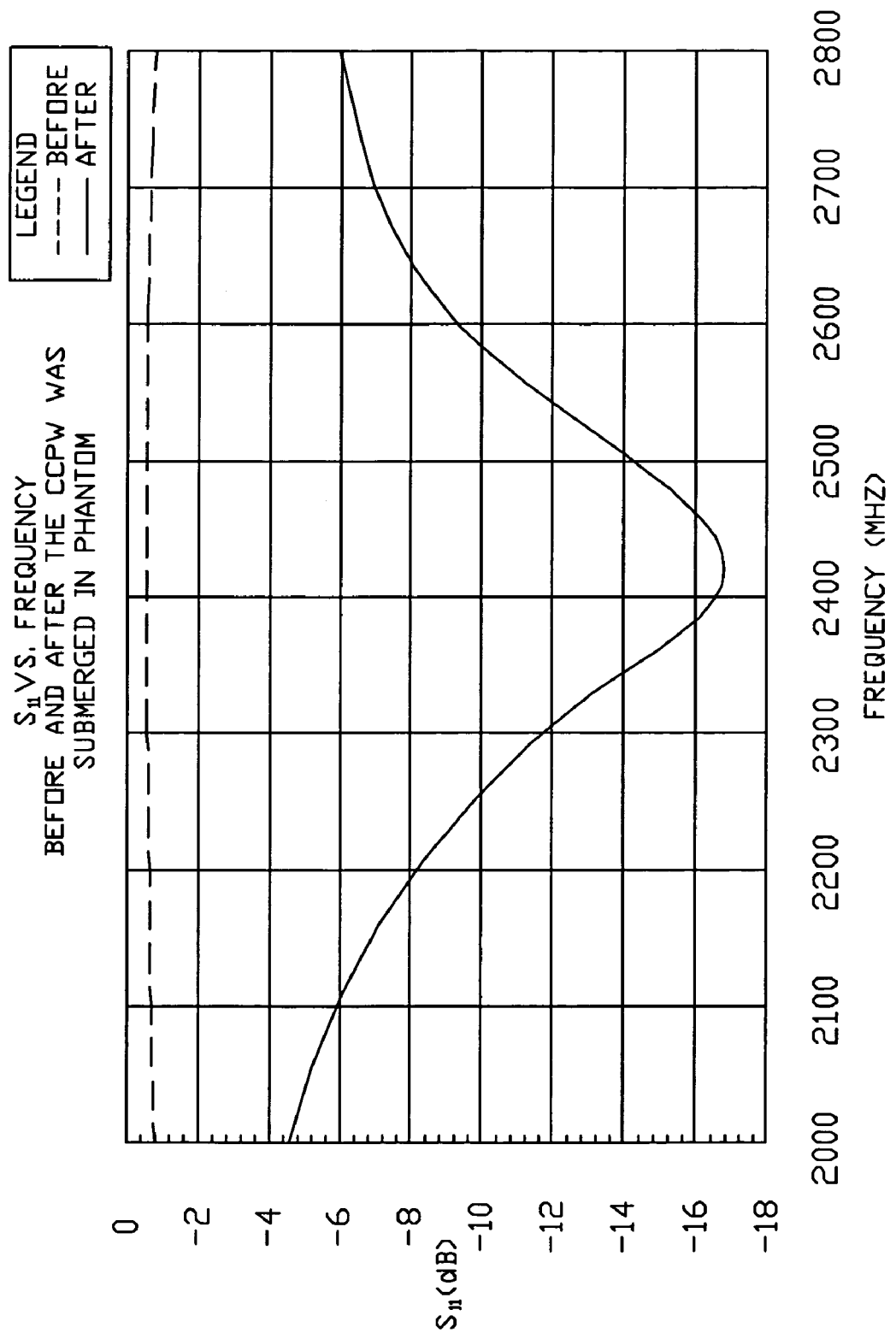
FIG. 7 is a graph of measured return loss with the catheter in air as compared to the catheter in phantom or surrogate biological material whereby it is seen that an excellent impedance match is provided at 2.41 GHz when the catheter is in the phantom biological material.

For antenna testing purposes, a biomedical tissue simulation material called phantom material was used. The phantom material was mixed so that it behaved like human tissue at the catheter operating frequency of 2.41 GHz. Each antenna prototype was tested in the phantom material to determine if power was being radiated into the material or simply reflected back due to impedance mismatches. Two potential sources of impedance mismatch are recognized: One is associated with the junction between transmission line or waveguide section 24 and radiating or antenna section 26. The other is associated with the match between the radiating section and the phantom material. Efficient antenna system performance is predicated upon minimizing the reflected power from all potential sources. The dimensions as given hereinbefore were developed using the mathematical model and several different designs until the best results were obtained as determined by various measurements. The measurements indicated in FIG. 7 are considered quite useful over a band extending from 2250 to 2575 MHz. The length of the antenna section may be altered to optimize performance for different bands.

FIG. 7 shows two different measurements were made of the catheter assembled as shown in FIG. 3. The results of FIG. 7 show measurement with the assembled catheter shown in air, and with the catheter submerged in the phantom material. It is readily seen that when the prototype catheter is in air, it reflects almost all the input power back to the source. However, once the catheter is submerged in the phantom material, a very good impedance match is obtained at 2.41 GHz. This indicates that most of the input power is being radiated into the phantom. More specifically, at 2.41 GHz, the return loss is −16.5 dB, which means that about 2.25% of the input power is reflected back to the source. This implies that (ignoring the negligible Ohmic losses in the circuit), 97.75% of the input power is radiated into the phantom material.

Figure 8:
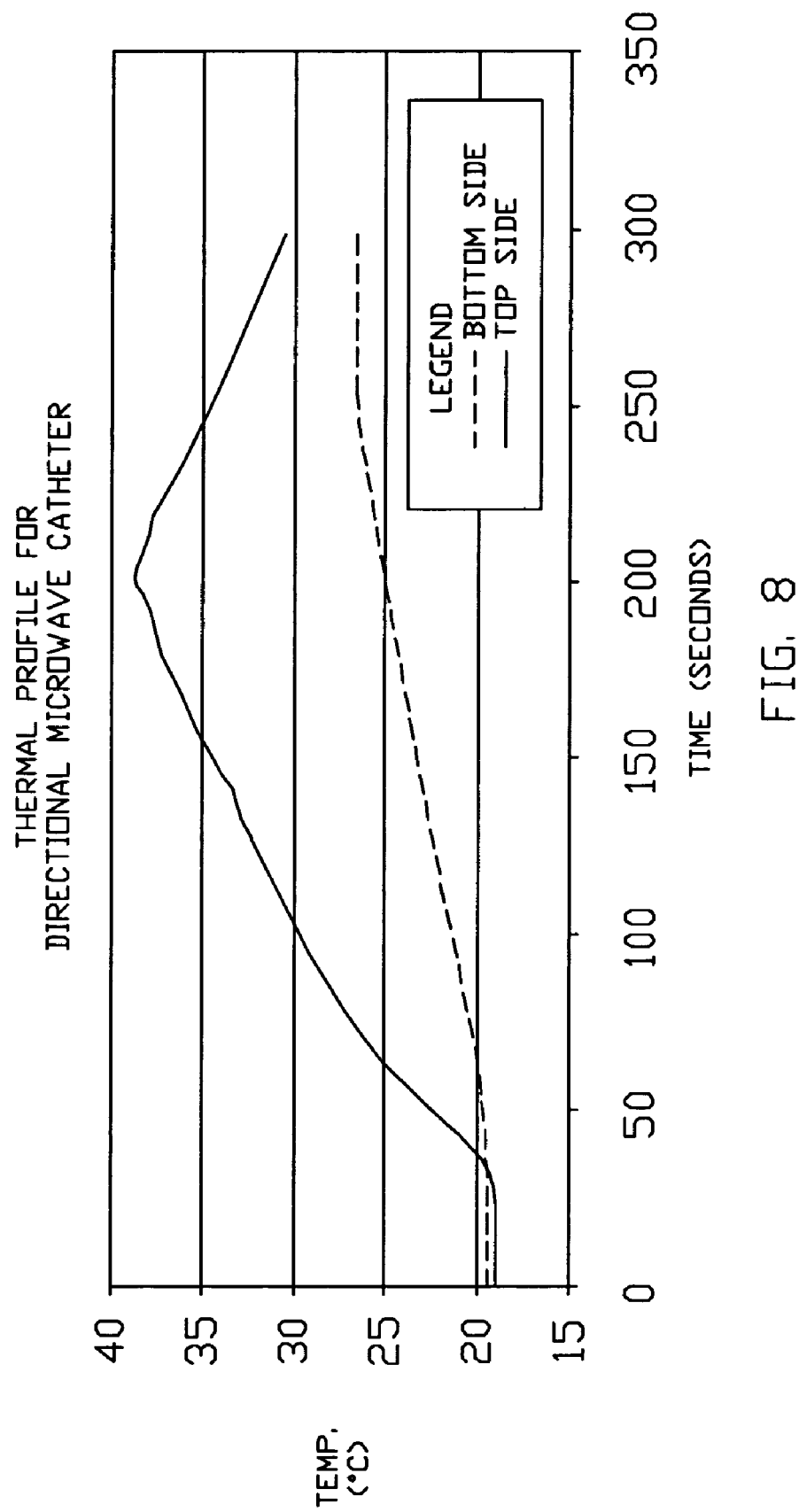
FIG. 8 is a graph showing a thermal profile for a directional microwave catheter in accord with possible embodiments of the present invention whereby the temperature of phantom material above the catheter is sufficient for ablation purposes while the temperature below the catheter remains low enough during heating to protect healthy tissue.

The directionality of the catheter assembled as shown in FIG. 3 when used in phantom material was tested with fiber-optic temperature probes spaced 3 mm above and 3 mm below the radiating microwave applicator 10. In this test, the catheter assembly was fed with 5 Watts of power at 2.41 GHz for 200 seconds. Results of the test are shown in FIG. 8. The test results shown in FIG. 8 demonstrate how the catheter directs power into the phantom as desired, heating the upper probe more than the lower probe. The upper probe measured a much higher temperature rise than the lower probe continuously until the power was removed (Time=200 seconds). This performance verifies that the directional catheter antenna allows a user to concentrate heat on a specific targeted area of tissue without excessively heating the surrounding healthy tissue. The cells in front of the antenna can be killed by the direct radiation while the cells behind the antenna will not receive a lethal dose.

Figure 9:
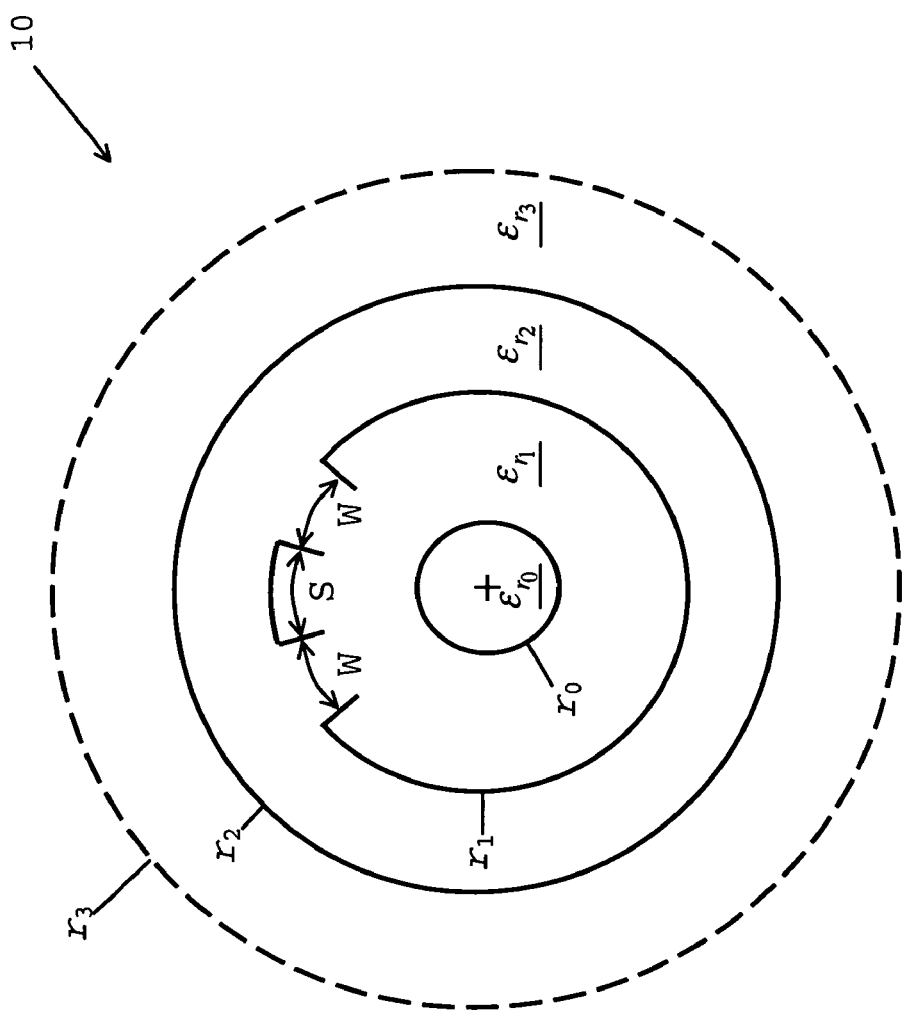
FIG. 9 is a diagram depicting mathematical variables and their relation to the microwave applicator components.

Referring to FIG. 9, equations are provided that describe dimensions, features, and operation of a multilayer substantially cylindrical coplanar waveguide with the many parameters which determine the characteristic impedance of the line as shown in the cross sectional drawing of FIG. 9.

The following equations were obtained and/or derived from references cited above ("Microstrip Lines and Slotlines," for determining parameters for multi-layer co-planar waveguides, and "Design of Nonplanar Microstrip Antennas and Transmission Lines," for determining parameters for co-planar waveguides on cylinders).

Width parameters for the center strip 12, or S, and the gap, W, between the center strip and the ground plane are determined given the dielectric constant, the radius of each of the layers, and the desired characteristic impedance. For the embodiment described herein, the target characteristic impedance was 50 Ohms.

To determine the characteristic impedance given the relevant parameters, the effective dielectric constant, $\epsilon_{\mathit{eff}}$ of the system, and the parameter $C^a$, which is the capacitance of the structure with the dielectric replaced by air, must be found first. In the following equations, $r_i$ is the outer radius of the $i^{th}$ layer wherein i is greater than or equal to 1 (FIG. 9), S and W are the width of the center conductor and gap, respectively (FIG. 9), and $\epsilon_0$ is the permittivity of air. The characteristic impedance is given as:

$$Z_C = \frac{120\pi\varepsilon_o}{C^a \sqrt{\varepsilon_{\mathit{eff}}}}, \qquad \text{Equation 1}$$

where $$C^a = 4\varepsilon_o \frac{K(k_a)}{K(k'_a)} \qquad \text{Equation 2}$$

with $$k'_a = \sqrt{1-k_a^2}, \text{ where} \qquad \text{Equation 2a}$$

$$k_a = \frac{S}{S+2W} \sqrt{\frac{1-(S+2W)^2/4r_1^2\pi^2}{1-S^2/4r_1^2\pi^2}}, \qquad \text{Equation 3}$$

and $$\frac{K(k_a)}{K(k'_a)} = \frac{\pi}{\ln\left[2\left(1+\sqrt{k'_a}\right)/\left(1-\sqrt{k'_a}\right)\right]}. \qquad \text{Equation 4}$$

Now that $C^a$ has been determined, the effective dielectric constant is determined. To do this, the filling factors, $q_i$, for each of the layers must be determined. Starting with layers 1 and 2, $$q_i = \frac{C^a_{si}}{C^a}, \qquad \text{Equation 5}$$

with $$C^a_{si} = 2\varepsilon_o \frac{K(k_i)}{K(k'_i)}, \qquad \text{Equation 6}$$

and $$k'_i = \sqrt{1-k_i^2} \qquad \text{Equation 7a}$$

$$k_i = \frac{\sinh(A_i S)}{\sinh(A_i(S+2W))} \sqrt{\frac{1-\frac{\sinh^2[A_i(S+2W)]}{\sinh^2(2A_i r_1 \pi)}}{1-\frac{\sinh^2(A_i S)}{\sinh^2(2A_i r_1 \pi)}}}, \qquad \text{Equation 7b}$$

and $$\frac{K(k_i)}{K(k'_i)} = \frac{\pi}{\ln\left[2(1+\sqrt{k'_i})/(1-\sqrt{k'_i})\right]} \qquad \text{Equation 7c}$$

where $$A_1 = \frac{\pi}{4 r_1 \ln(r_1/r_0)}, \qquad \text{Equation 8a}$$

and $$A_2 = \frac{\pi}{4 r_1 \ln(r_1/r_2)}. \qquad \text{Equation 8b}$$

wherein $r_0$ is the inner radius of layer 1. For $A_i$ wherein i is greater than or equal to 3, the conformal mapping technique, as outlined in stated references, is used to extend the approach for an arbitrary number of layers.

Once the filling factors are determined for layers 1 and 2, which are the layers directly below and above the center strip and ground plane, respectively, the filling factors for the innermost and outermost layers must be calculated. In this example, the innermost and outermost layers in this application are air and biological tissue, respectively. The filling factor for the innermost layer is $$q_0 = \frac{C^a/2 - C^a_{s1}}{C^a}, \qquad \text{Equation 9}$$

and the filling factor for the outermost layer is $$q_3 = \frac{C^a/2 - C^a_{s2}}{C^a}. \qquad \text{Equation 10}$$

When all of the filling factors are determined, a check is performed to make sure that the sum of all the filling factors is equal to one. To determine the effective dielectric constant, one calculates $$\varepsilon_{\mathit{eff}} = \sum_{i=1}^{n} q_i \varepsilon_{ri}. \qquad \text{Equation 11}$$

where $\varepsilon_{ri}$ is the relative permittivity for the $i^{th}$ layer.

Figure 10:
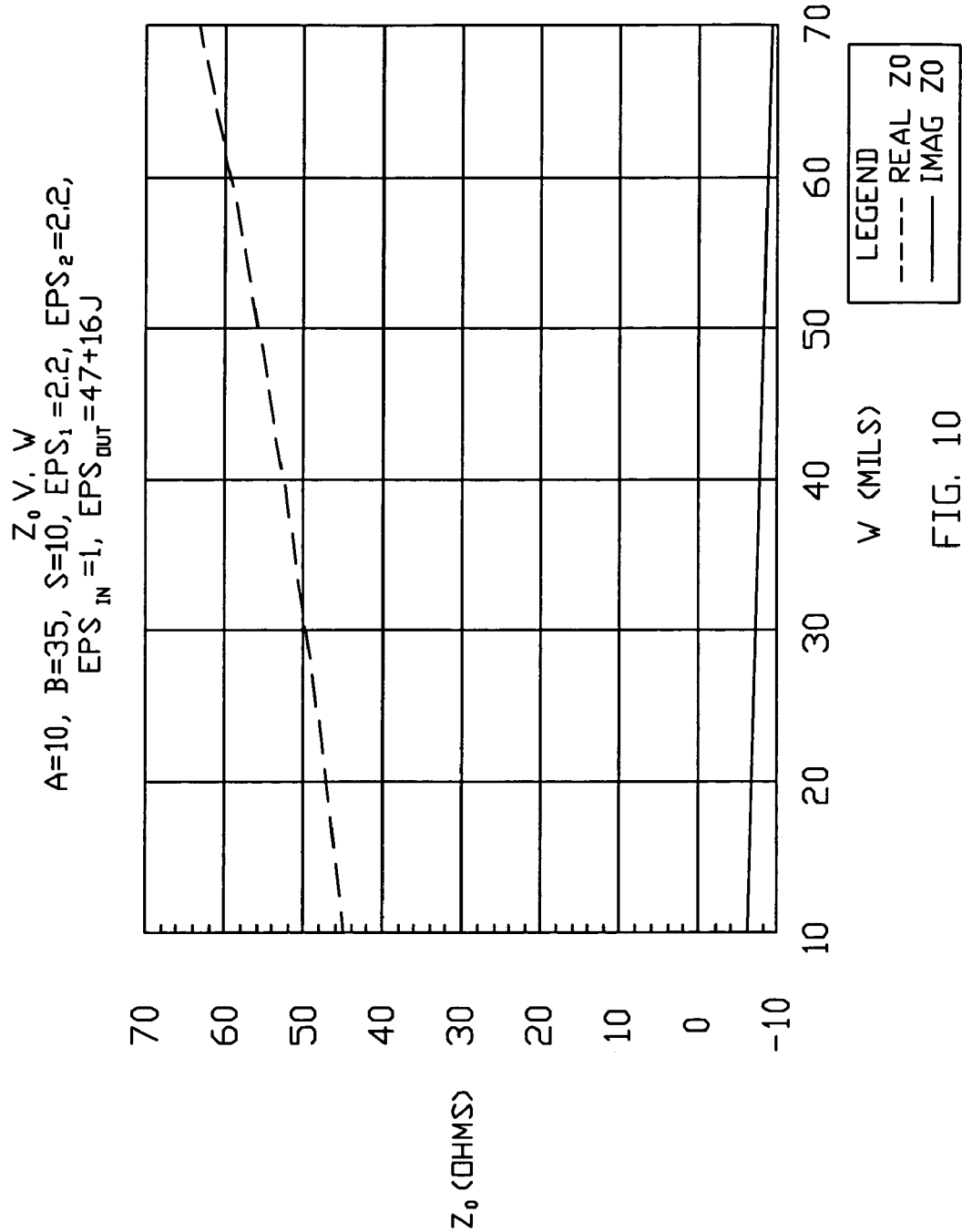
FIG. 10 is a graph based on the mathematical model of FIG. 9 for the characteristic impedance of a transmission line section or waveguide section with respect to gap width, W, between the center strip and the ground plane conductors in accord with possible embodiments of the present invention.

Applying Equation 11 and Equation 2 to Equation 1, an approximate characteristic impedance of the line is obtained. FIG. 10 shows a plot of some results for the characteristic impedance vs. gap width, W. From FIG. 10 it can be seen that the range of gap width values, W, between 20 and 40 results in a characteristic impedance near 50 Ohms with other parameters as stated in FIG. 10.

Figure 11:
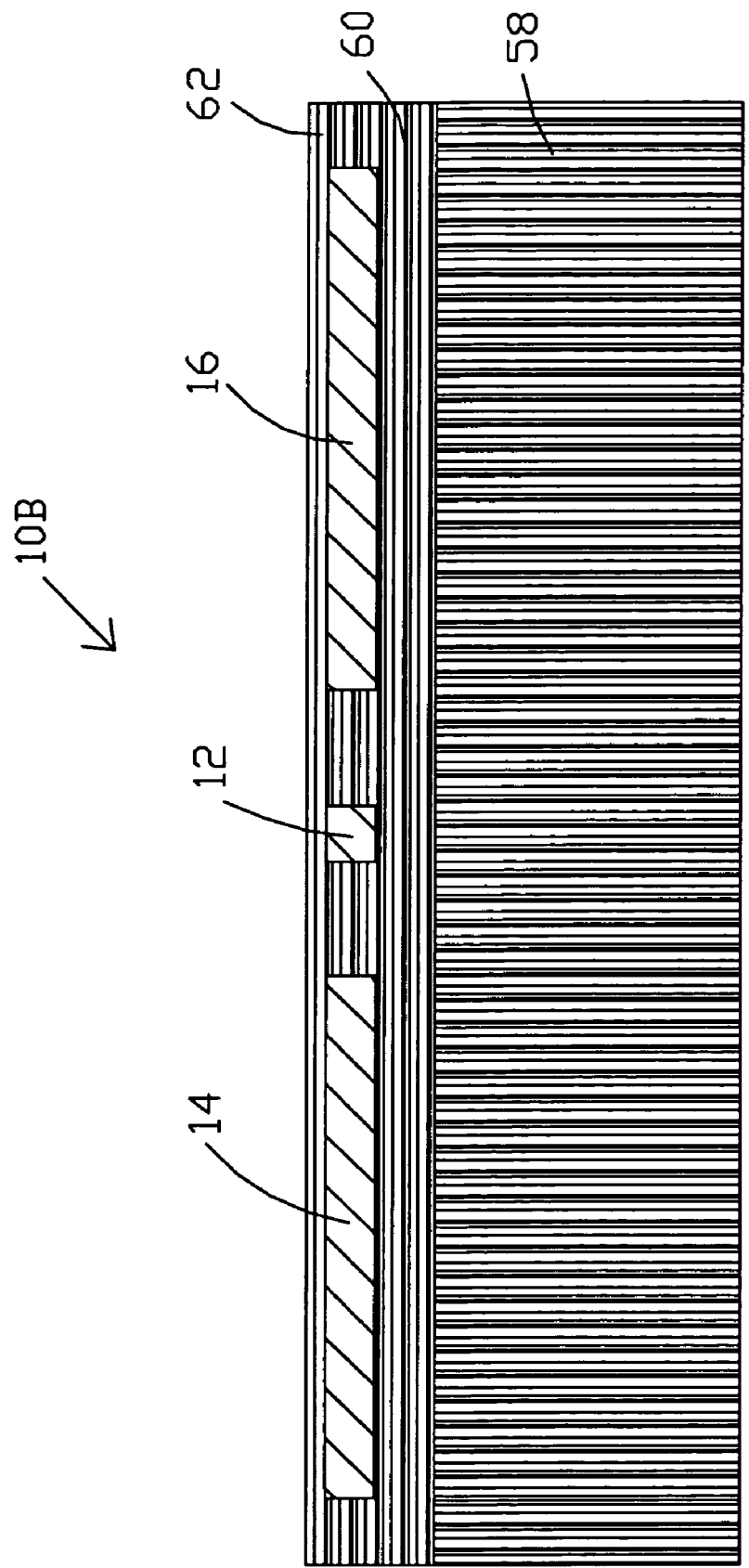
FIG. 11 is an elevational view, in cross-section, showing a coplanar waveguide and the various layers of materials including outer coverings that might be utilized in conductors in accord with possible embodiments.

FIG. 11 shows a multilayered coplanar waveguide 10B with material 62 above conductors 12, 14, and 16. The same or a different material 60 may surround conductors and support conductors 12, 14, and 16. Another layer 58 may or may not also be utilized.

Thus, different numbers of layers may or may not be utilized with the various contributions of layers being determined as the above. In a presently preferred embodiment, the layers other than conductors 12, 14, and 16 are non-conductors. The phantom material is not shown.

While a cylindrical model is utilized in the preferred embodiment, the internal cross-sectional arch shape of ground conductors 14 and 16, and the spacing between ground conductors 14 and 16 can be altered by using elliptical and other curvatures, if desired. The relative width or arc-length of the cross-section of ground conductors 14 and 16 can also be varied. These can be used to affect the depth of heating and the energy directivity. Moreover, the interior of microwave applicator 10 can be hollow to permit the introduction of cooling fluid if desired for the particular application to reduce the temperature directly adjacent conductors 12, 14, or 16, any of which may include tissue which is preferably not heated, in some cases.

In summary, the present invention provides, in one possible embodiment, a substantially cylindrical miniaturized microwave antenna intended for biomedical applications such as, for example, radiation induced hyperthermia through catheter systems. One key feature of this antenna is that it possesses azimuthal directionality despite its small size. One embodiment of the present invention has an outer diameter of about 0.095" (2.4 mm) but because of the design, embodiments with even smaller diameter exist. The directionality of the miniaturized microwave antenna permits targeting of certain tissues while limiting thermal exposure of adjacent tissue when operating within small apertures. Accordingly, the antenna described herein was designed to provide a means for radiating, with azimuthal directionality, into a biological medium. The antenna is sufficiently small to function as a catheter or syringe antenna.

In one embodiment, the antenna makes use of connection shown generally at location 46 from flexible coaxial cable 38 to a generally circular transmission line or waveguide section 24. A junction or beginning of taper section 34 provides an impedance match between waveguide section 24 and antenna section 26. Thus transmission line or waveguide section 24 guides the RF/microwave radiation along the microwave applicator 10, and the ground portion of the microwave applicator 10 is tapered as indicated at 34 to a thin ground strip on the back side of antenna section 26. The increased gap size results in extension of the electromagnetic field into the biological medium where power is absorbed. The remaining ground strip on the back side serves to restrict radiation on that side. Excellent impedance matching was demonstrated with the prototype submerged in a phantom material simulating human tissue at 2.4 GHz. Also, the directionality was verified by means of nonconductive thermal probes placed in the phantom surrounding the antenna. The directionality may be tailored to some extent based on characteristics of the antenna. Also, a variation of the design, as indicated generally at 46 in FIG. 4, is provided to electromagnetically couple from center conductor 42 to center strip 12. This approach has the advantage of easing fabrication. Some possible applications include hyperthermia for microwave angioplasty and microwave hyperthermia as a substitute for vertebroplasty.

In one embodiment, shown in FIGS. 12, 12A and 12B, the waveguide section (FIG. 12A) of the device consists of ground conductors shown as 14 and 16, in which ground conductors 14 and 16 are a continuous conductive section, and a single slot exists along the waveguide such that the electromagnetic field is guided by the slot. The antenna portion (FIG. 12B) likewise consists of a single slot in a continuous conductive section, and, in an embodiment, the antenna slot 71 in the antenna portion (FIG. 12B) is wider than the waveguide slot 70 in the waveguide section (FIG. 12A). There also may exist a taper section 34 in the slot width between the waveguide section (FIG. 12A) and the antenna portion for the purpose of matching the characteristic impedances of each of these sections. In an embodiment, the antenna slot 71 in the antenna portion (FIG. 12B) is shorted by a conductive strip 72, as illustrated in FIG. 12.

As used herein, waveguide and transmission line may be used interchangeably. As well, microwaves and radiofrequency waves are used interchangeably herein. Accordingly, section 24 may be referred to as either a waveguide or transmission line and may be utilized for connecting electromagnetic power between a source and antenna section 26.

Thus, while the preferred embodiment of the miniature directional microwave applicator is disclosed in accord with the law requiring disclosure of the presently preferred embodiment of the invention, other embodiments of the disclosed concepts may also be used. Therefore, the foregoing disclosure and description of the invention are illustrative and explanatory thereof, and various changes in the method steps and also the details of the apparatus may be made within the scope of the appended claims without departing from the spirit of the invention.

What is claimed is:

1. A miniature microwave applicator, comprising:
   an elongate structure, said elongate structure comprising a surface;
   a substantially non-radiating portion of said elongate structure comprising,
      a waveguide mounted on or closely adjacent to said surface of said elongate structure and extending along said elongate structure, said waveguide defining at least one waveguide gap therebetween, said at least one waveguide gap each comprising a waveguide gap width; and
   a radiating portion of said elongate structure, comprising,
      an antenna conductor and one or more antenna elements mounted on or closely adjacent to said surface of said elongate structure, said antenna conductor and said one or more antenna elements defining an antenna gap which is continuous with said waveguide gap, said antenna gap comprising an antenna gap width, said antenna gap width being greater than said waveguide gap width.

2. The applicator of claim 1, further comprising an impedance matching section positioned between said substantially non-radiating portion and said radiating portion, said impedance matching section defining an impedance matching gap width which varies in width along a length of said impedance matching section.

3. The applicator of claim 1, wherein said waveguide comprises a center conductor and substantially continuous second and third conductors which extend along said substantially non-radiating portion and into said radiating portion where they become said antenna conductor and said one or more antenna elements.

4. The applicator of claim 3, wherein said second and third conductors are electrically shorted to each other to effectively provide a single conductor.

5. The applicator of claim 3, wherein said second conductor and said third conductor are decreased in width within said radiating portion.

6. The applicator of claim 3, further comprising an impedance matching section between said substantially non-radiation portion and said radiating portion such that respective widths of said second and third conductors varies within said impedance matching section.

7. The applicator of claim 1, wherein said at least one waveguide gap width is substantially constant within said substantially non-radiating portion.

8. The applicator of claim 1, wherein said at least one waveguide gap comprises first and second waveguide gaps, said first and second waveguide gaps being equal in width.

9. The applicator of claim 1, wherein said elongate structure is rounded and comprises substantially non-conductive material.

10. The applicator of claim 9, wherein said elongate structure further comprises substantially non-conductive surface material, said waveguide being mounted on or within said substantially non-conductive surface material.

11. The applicator of claim 1, wherein said waveguide comprises a center conductor which is continuous with said antenna conductor and which extends continuously along said substantially non-conductive material from said non-radiating portion to said radiating portion.

12. The applicator of claim 1, further comprising a coaxial cable and an electrical connection between said substantially non-radiating portion and said coaxial cable.

13. The applicator of claim 12, wherein said coaxial cable comprises an outer coaxial conductor and an inner conductor, wherein said waveguide comprises a center conductor, said inner conductor being shorted to said center conductor.

14. The applicator of claim 12, wherein said coaxial cable comprises an outer coaxial conductor and an inner conductor, wherein said waveguide comprises a center conductor, said inner connector being electromagnetically coupled to said center conductor.

15. The applicator of claim 1, further comprising a substantially non-conductive outermost covering for said non-radiating portion and said radiating portion, said substantially non-conductive outermost covering being positioned radially outwardly of said first waveguide conductor and said one or more waveguide conductors.

16. The applicator of claim 1, wherein said antenna conductor is spaced sufficiently from said one or more antenna elements such that said radiating portion thereby acts as a microwave radiator, said one or more antenna elements being substantially arc-shaped when viewed in cross-section.

17. The applicator of claim 1, wherein said antenna conductor of said radiating portion is spaced sufficiently from said one or more antenna elements to be operable for radiation of microwave energy, said one or more antenna elements being operable to direct microwaves radiated by said antenna conductor predominately in an azimuthal direction with respect to said antenna conductor.

18. The applicator of claim 1,
wherein said radiating portion radiates energy over a predetermined operating frequency band;
wherein said radiating portion is characterized by a radiating portion length that results in said radiating portion being substantially resonant over said operating frequency band.

19. The applicator of claim 18, wherein said radiating portion length is such that said operating frequency band coincides with the first resonance of said radiating portion.

20. The applicator of claim 1, wherein said radiating portion radiates energy into surrounding biological material and is characterized by a radiating portion length such that any of said energy reflected at the end of said radiating portion is substantially radiated into or absorbed by said surrounding biological material prior to reaching or returning to said waveguide portion.

* * * * *